(12) United States Patent
Sasayama et al.

(10) Patent No.: US 6,693,229 B2
(45) Date of Patent: Feb. 17, 2004

(54) INBRED BROCCOLI LINE VBC-406

(75) Inventors: Junichi Sasayama, Kakegawa (JP); Shigetoshi Kobayashi, Tsu (JP)

(73) Assignee: Sakata Seed America, Inc., Morgan Hill, CA (US)

( * ) Notice: Subject to any disclaimer, the term of this patent is extended or adjusted under 35 U.S.C. 154(b) by 0 days.

(21) Appl. No.: 09/951,982

(22) Filed: Sep. 11, 2001

(65) Prior Publication Data

US 2003/0093841 A1 May 15, 2003

(51) Int. Cl.⁷ .............. A01H 4/00; A01H 5/00; A01H 5/10; A01H 1/00
(52) U.S. Cl. .............. 800/306; 800/260; 435/410; 435/421; 435/430.1
(58) Field of Search ............ 435/4, 410, 419, 435/421, 430, 430.1; 800/260, 264, 265, 266, 267, 268, 271, 274, 278, 287, 298, 299, 301, 302, 306

(56) References Cited

U.S. PATENT DOCUMENTS 5,523,520 A * 6/1996 Hunsperger et al. ........ 435/410

OTHER PUBLICATIONS

Bennetzen et al. 1992. Approaches and progress in the molecular cloning of plant disease resistance genes. Genetic Engineering 14:99–124.*

Cheung et al. 1997. Conservation of S–locus for self incompatibility in *Brassica napus* (L.) and *Brassica oleracea* (L.). Teor. Apll. Genet. 95:73–82.*

Earle et al. 1994. Cold–tolerant Ogura CMS Brassica vegetables for horticultural use. Cruciferae Newsletter 16:80–81.*

Eshed et al. 1996. Less–than–additive epistatic interactions of quantitative trait loci in tomato. Genetics 143:1807–1817.*

Kao et al. 1990. Efficient plant regeneration from hypocotyl protoplasts of broccoli (*Brassica oleracea* L. ssp. italica Plenck). Plant Cell Reports 9:311–315.*

Kott et al. 1990. The role of biotechnology in canola/rapeseed research. Pp. 47–78, In:Rapeseed Production, Nutrition, and Technology. Van Reinold, New York.*

Kraft et al. 2000. Linkage disequilibrium and fingerprinting in sugar beet. Theor. Appl. Genet. 323–326.*

Pang et al. 1992. Expression of a gene encoding scorpion insectotoxin peptide in yeast, bacteria, and plants. Gene 116:165–172.*

* cited by examiner

Primary Examiner—David T. Fox
Assistant Examiner—Cynthia Collins
(74) Attorney, Agent, or Firm—Jondle & Associates PC

(57) ABSTRACT

Inbred broccoli line, designated VBC-406 is disclosed. The invention relates to the seeds of inbred broccoli line VBC-406, to the plants of inbred broccoli line VBC-406, and to methods for producing a broccoli plant produced by crossing the inbred line VBC-406 with itself or another broccoli line. The invention further relates to hybrid broccoli seeds and plants produced by crossing the inbred line VBC-406 with another broccoli line.

10 Claims, No Drawings

INBRED BROCCOLI LINE VBC-406

BACKGROUND OF THE INVENTION

This invention relates to a new and distinctive broccoli inbred line, designated VBC-406. There are numerous steps involved in the development of any new and novel desirable germplasm with superior combining ability. Plant breeding begins with the analysis and definition of problems and weaknesses of the current germplasm, the establishment of program goals, and definition of specific breeding objectives. The next step is selection of germplasm that posses the traits to meet the program goals and the best breeding method to reach those goals. The objective is to combine in a single variety or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the cultivar (variety) used commercially (e.g. $F_1$ hybrid, pureline). The complexity of inheritance influences choice of breeding method. A most difficult task is the identification of individuals that are genetically superior, because for most traits other confounding plant traits or environmental factors masks the true genotypic value. One method of identifying a superior plant is to observe its performance relative to other experimental plants and to a widely grown standard cultivar. If a single observation is inconclusive, observation in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines by selfing followed by selection of desired phenotypes sometimes utilizing anther, microspore and ovule culture to speed up and improve selection efficiency.

The goal of plant breeding is to develop new, unique, and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Description of breeding methods that are commonly used for different traits and crops can be found in one of several reference books. (e.g. Allard, 1960; Simmonds, 1979; Sneep et. al., 1979; Fehr, 1987).

Proper testing and evaluation should detect any major faults and establish the level of superiority or improvement over current cultivars. In addition to showing superior performance, there must be a demand for a new cultivar that is compatible with industry standards or which creates a new market. For seed-propagated cultivars, it must be feasible to maintain the inbred lines and produce seed easily and economically.

Broccoli is a new crop in North, South and Central America, Northern Europe and Asia. The introduction of hybrid cultivars in the 1960's provided a magnitude increase in yield, holding ability, plant uniformity, expanded growing seasons and large-scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea*, Italica group) belongs to the mustard family. All *Brassica oleracea* will cross-pollinate. Insect vectors, most common of which is the honeybee effect pollination. Broccoli, like most other Brassica, has a genetic characteristic of self-incompatibility, which encourages cross pollination resulting in higher levels of variability. Variability in populations is desired for wide adaptation and survival. Broccoli breeding populations can be inbred or backcrossed for 8 to 9 generations and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross-pollinated species. This breeding system in nature has been utilized by man in $F_1$ hybrid breeding, especially in Brassica vegetables (Tsunoda et al., chapter 13).

Cytoplasmic male sterility (CMS) is another method used in Brassica vegetables species to produce $F_1$ hybrids. This method of producing hybrids in Brassica is a more recent development compared to self-incompatibility. A genetic mutation contained in the cytoplasm (mitochondria) is responsible for the lack of production of pollen. In Brassica, the cytoplasm has commonly been identified in and transferred from "Ogura"-type radish (Ogura, 1968). The major advantage of CMS over self-incompatibility is that under normal conditions, no pollen is produced in the female parent. This results in the production of 100% hybrid seed. Under certain stressful growth conditions, however, it may be possible to produce small amounts of fertile pollen in CMS plants. Brassica inbreds containing CMS (sterile "A" lines) are maintained by continued hybridization to their normal (fertile) counterpart inbred, commonly referred to as a "B" line.

The plants associated with the Brassica group have been familiar to mankind since ancient times, and always of great agricultural importance. Brassica is a major food species worldwide. Brassica species have a general adaptation for cool climate growing conditions. Therefore, adaptation has occurred for summer growing conditions with cool to moderate climates and for winter growing conditions in warmer or tropical locations.

SUMMARY OF THE INVENTION

The invention comprises a novel inbred broccoli line, designated VBC-406. This invention thus relates to the seeds of inbred broccoli line VBC-406, to the plants of inbred broccoli line VBC-406, to methods used for controlling pollination when making hybrid seed with VBC-406, and to methods for producing a broccoli plant by crossing the inbred broccoli line VBC-406 with itself or another broccoli line. This invention further relates to hybrid broccoli seeds and plants produced by crossing the inbred line VBC-406 with another broccoli line.

DETAILED DESCRIPTION OF THE INVENTION

In the description and tables, which follow, a number of terms are used. In order to provide a clear and consistent understanding of the specification and claims, including the scope to be given such terms, the following definitions are provided.

Plant Height: Plant height is measured in centimeters from the soil line to the top of the leaves.

Head Height: Head height is measured in centimeters from the soil line to the top of the head.

Leaf Width: Leaf width is measured in centimeters at the midpoint of the plant including the petiole.

Leaf Length: Leaf length is measured in centimeters from the midpoint of the plant including the petiole.

Head Diameter: Head Diameter is measured at the widest diameter of the head (from overhead) in centimeters.

Head Depth: Head Depth is measured in centimeters from the top of the head to the lowermost florets.

Stem Diameter: Stem diameter is measured in centimeters and is taken at a point just below the head.

Maturity: Plants are considered mature when the head and stem have developed to the fresh market maturity stage.

Yield: The yield is the weight in grams for a harvested broccoli head or floret cluster.

Overall Rating Score: This Overall Rating Score is rated on a scale of 1 to 5. A score of 5 indicated an excellent overall rating. A score of 3.0 indicates average, and a score of 1 indicates poor.

Color: Color means the color of the head at maturity.

Field Holding Ability: Field Holding Ability means the ability of a plant to maintain good head quality (i.e. small, firm, green heads) after the optimal harvest date.

Disease and Insect Ratings: Disease and Insects are rated on a scale of 1 to 5. A score of 5 indicates severe damage. A score of 3.0 indicates moderate damage, and a score of 1 indicates no damage.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

Inbred broccoli VBC-406 is a heading broccoli (*Brassica oleracea* Italica group) with superior characteristics, and provides an excellent parental line in crosses for producing first generation ($F_1$) hybrid broccoli.

Inbred line VBC-406 was developed from the 1991 initial cross at Kimitsu, Japan, of line IU-9 to a source of CMS herein referred to "Cabbage, Radish, MS-2". The CMS source "Cabbage, Radish, M-2" is protected under U.S. Pat. No. 56,560,559. IU-9 is an inbred resulting from a cross between proprietary inbred lines UL X B-24 in the spring of 1974, Kimitsu, Japan. Beginning in 1992 the IU-9 backcross breeding was done in Salinas, Calif., USA. From 1992 to 1997 seven backcross generations were completed to recover the IU-9 background. Confirmation of uniformity, stability for important traits and combining ability were determined from 1997 to 1998 in Kakegawa, Japan and Salinas, Calif., USA, resulting in inbred broccoli VBC-406.

The inbred has shown uniformity and stability for all traits, as described in the following variety description information. The line has been increased and maintained by pollination with fertile inbred line VBC-406 non-CMS with continued observation for uniformity.

The inbred broccoli line VBC-406 has the following morphologic and other characteristics. The data were collected in the spring of 2001 in Salinas, Calif., USA.

Variety Description Information

MATURITY: Late, approximately 95 days from sowing

PLANT CHARACTERISTICS:

Habit: Spreading

Plant Heights: 23 cm

Leaves: 17 cm average length at mid-point of plant (minus petiole), 14 cm width at the mid-point of the plant, 2:1 ratio length to width Leaf Margins: wavy Veins: thin Petiole Attachment: Petiolate (petiole 13 cm in length)

Anthocyanin Coloration: Absent

Inflorescence: Small flower bud, yellow flowers, few side sprouts after main head is harvested, 11 cm center head diameter, 8 cm head depth, 4 cm stem diameter at base of head, medium center head compactness, center head color medium green.

This invention is also directed to methods for producing a broccoli by crossing a first parent broccoli plant with a second parent broccoli plant, wherein the first or second broccoli plant is the inbred broccoli from the line VBC-406. Further, both first and second parent broccoli plants may be from the inbred line VBC-406. Therefore, any methods using the inbred broccoli line VBC-406 are part of this invention; selfing, backcrosses, hybrid breeding, and crosses to populations. Any plants produced using inbred broccoli line VBC-406 as a parent are within the scope of this invention. Advantageously, the inbred broccoli line is used in crosses with other broccoli varieties to produce first generation ($F_1$) broccoli hybrid seed and plants with superior characteristics.

As used herein, the term "plant" includes plant cells, plant protoplasts, plant cells of tissue culture from which broccoli plants can be regenerated, plant calli, plant clumps, and plant cells that are intact in plants or parts of plants, such as pollen, flowers, seeds, stalks, stumps, leaves and the like. Thus, another aspect of this invention is to provide for cells, which upon growth and differentiation produce the inbred broccoli VBC-406.

When the term inbred broccoli plant is used in the context of the present invention, this also includes any single gene conversions of that inbred. The term single gene converted plant as used herein refers to those broccoli plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental broccoli plants for that inbred. The parental broccoli plant which contributes the gene for the desired characteristic is termed the nonrecurrent or donor parent. This terminology refers to the fact that the nonrecurrent parent is used one time in the backcross protocol and therefore does not recur. The parental broccoli plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. No. 5,777,196, the disclosure of which is specifically hereby incorporated by reference.

A further aspect of the invention relates to tissue culture of broccoli plants designated VBC-406. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, heads, leaves, stalks, roots, root tips, anthers and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as anthers, has been used to produce regenerated plants. (See U.S. Pat. No. 5,445,961 and U.S. Pat. No. 5,322,789, the disclosures of which are incorporated herein by reference).

TABLE

In Tables 1–4 that follow, the traits and characteristics of inbred broccoli line VBC-406 is given in hybrid combination. The data collected on hybrids containing inbred broccoli line VBC-406 as one parent is presented. The table presents overall rating scores and additional characteristics. VBC-406 was tested in several hybrid combinations at different locations over a number of years. Information about these hybrids, as compared to several check hybrids, is presented. Column 2 shows the overall rating, which ranges from 1–5, with 5 being the best overall rating. Column 3 lists various characteristics of the specific hybrid.

TABLE 1

Combining ability of inbred line VBC-406. Plants were grown at Kakegawa Research Station in Kakegawa, Japan.

| Variety | Overall Rating | Comments |
| --- | --- | --- |
| VBC-406 × Line 35 | 4.0 | Good smooth dome shape, erect plant habit. |
| Line G × Line 35 | 3.0 | Lodging, irregular shape, semi-dome shape. |
| VBC-406 × Line Y | 4.0 | Late maturity, very good dome shape. |
| Line KU × Line Y | 3.0 | Vigorous plant, tight head, semi-dome shape. Smooth semi-dome shape, dark green, and |
| VBC-406 × Line D | 3.5 | good plant habit. |
| Line NU × Line D | 2.0 | Flat head, big bead size. |

TABLE 2

Combining ability of inbred line VBC-406. Plants were grown at Salinas Research Station in Salinas, California.

| Variety | Overall Rating | Comments |
| --- | --- | --- |
| VBC-406 × Line H | 3.2 | Early maturity, round, smooth shape, mid-small bead, semi-dome. |
| Line G × Line H | 2.9 | Vigorous plant, bad uniformity, bit irregular shape, semi-flat, mid-large bead. |
| Line H × Line S | 2.8 | Mid-small bead, bit lumpy, irregular shape, semi-dome, uneven bead. |
| VBC-406 × Line D | 3.2 | Late, round smooth shape, medium bead, semi-flat, and some heat damage. |
| Line D × Line S1 | 3.0 | Mid-small bead, bit irregular shape, pale color, semi-dome, dwarf plant. |
| Line D × Line KH | 2.5 | Irregular shape, mid-small bead, uneven bead, many cat eye, and lumpy, bad shape. |

TABLE 3

Combining ability of inbred line VBC-406. Plants were grown at Salinas Research Station in Salinas, California.

| Variety | Overall Rating | Comments |
|---|---|---|
| VBC-406 × Line D | 3.3 | Round smooth head, mid-large bead, semi-dome, bit loose head. |
| Line D × Line S1 | 2.2 | Mid-small bead, bit irregular shape, semi-flat, pale color, bit loose head. |
| Line D × Line 35 | 2.2 | Loose head, uneven bead, pale color, mid-small bead, and semi-flat. |

TABLE 4

Combining ability of inbred line VBC-406. Plants were grown at Salinas Research Station in Salinas, California.

| Variety | Overall Rating | Comments |
|---|---|---|
| VBC-406 × Line L2 | 3.9 | Dome, not so vigorous, round good shape, good uniformity, bit pale color, smooth head. |
| Line L2 × Line S1 | 2.8 | Round smooth head, good shape, uneven bead, good uniformity, loose head, dome. |
| Line L2 × Line K8 | 2.7 | Mid-large bead, round smooth head, semi-dome, good uniformity but a bit loose. |
| VBC-406 × Line L3 | 3.8 | Late, dwarf, tight, round smooth dome head, small bead, bad uniformity. |
| Line L3 × Line S1 | 2.8 | Mid-small bead, semi-dome, bit loose, uneven bead, open habit, round smooth head. |
| Line L3 × Line O | 2.5 | Less vigor, lumpy, small bead, small head, dwarf plant. |
| VBC-406 × Line K4 | 3.8 | Mid-small bead, loose, uneven bead, round smooth good shape, semi-dome. |
| Line K4 × Line K2 | 3.2 | Mid-small bead, uneven bead, dome head, smooth round shape, tight, late. |

In Table 5 that follows, the traits and characteristics of inbred broccoli line VBC-406 are shown. Table 5 represents overall mean scores for each characteristic. Column 1 shows the plant height, column 2 shows the head height. Columns 3 and 4 are leaf width and length. Columns 5 and 6 indicate the head diameter and depth and column 7 indicates the stem diameter. All data is in centimeters.

TABLE 5

Characteristics of VBC-406.

| Plant Ht. | Head Ht. | Leaf Width | Leaf Length | Head Diameter | Head Depth | Stem Diameter |
|---|---|---|---|---|---|---|
| 23 cm | 23 cm | 14 cm | 17 cm | 11 cm | 8 cm | 4 cm |

Deposit Information

A deposit of the Sakata Seed America, Inc. proprietary inbred broccoli line VBC-406 disclosed above and recited in the appended claims has been made with the American Type Culture Collection (ATCC), 10801 University Boulevard, Manassas, Va. 20110. The date of deposit was Aug. 15, 2003. The deposit of 2,500 seeds were taken from the same deposit maintained by Sakata Seed America, Inc. since prior to the filing date of this application. All restrictions upon the deposit have been removed, and the deposit is intended to meet all of the requirements of 37 C.F.R. §1.801–1.809. The ATCC accession No. PTA-5404. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A broccoli seed designated VBC-406, wherein a sample of said seed has been deposited under ATCC Accession No. PTA-5404.

2. A plant, or its parts, produced by growing the seed of claim 1.

3. Pollen of the plant of claim 2.

4. An ovule of the plant of claim 2.

5. A broccoli plant, or parts thereof, having all of the physiological and morphological characteristics of the broccoli plant of claim 2.

6. Tissue culture of the seed of claim 1.

7. A broccoli plant regenerated from the tissue culture of claim 6, wherein said broccoli plant is capable of expressing all the physiological and morphological characteristics of inbred broccoli line VBC-406.

8. Tissue culture of regenerable cells of the plant, or its parts, of claim 2, wherein said tissue culture is selected from the group consisting of protoplasts and calli wherein the regenerable cells are derived from embryos, meristematic cells, pollen, leaves, anthers, roots, root tips, flowers, seeds, stems or florets.

9. A broccoli plant regenerated from the tissue culture of claim 8, wherein said broccoli plant is capable of expressing all the physiological and morphological characteristics of inbred broccoli line VBC-406.

10. A method for producing a F1 broccoli seed comprising crossing a first parent broccoli plant with a second parent broccoli plant and harvesting the resultant F1 hybrid broccoli seed, wherein said first or second parent broccoli plant is the broccoli plant of claim 2.

* * * * *